(12) United States Patent
Sternal et al.

(10) Patent No.: US 9,078,596 B2
(45) Date of Patent: Jul. 14, 2015

(54) IMAGING APPARATUS AND IMAGING METHOD

(71) Applicant: CANON KABUSHIKI KAISHA, Tokyo (JP)

(72) Inventors: Marek Sternal, Toruń (PL); Kenji Muto, Fujisawa (JP); Krzysztof Wiśniewski, Toruń (PL)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 13/972,842

(22) Filed: Aug. 21, 2013

(65) Prior Publication Data

US 2014/0063450 A1 Mar. 6, 2014

(30) Foreign Application Priority Data

Aug. 30, 2012 (JP) ................................ 2012-190597

(51) Int. Cl.
*A61B 3/10* (2006.01)
*A61B 3/00* (2006.01)
*A61B 3/12* (2006.01)

(52) U.S. Cl.
CPC .............. *A61B 3/102* (2013.01); *A61B 3/0008* (2013.01); *A61B 3/12* (2013.01)

(58) Field of Classification Search
CPC .............................. A61B 3/102; A61B 3/0008
USPC ......................................................... 351/206
See application file for complete search history.

(56) References Cited

U.S. PATENT DOCUMENTS

| | | | |
|---|---|---|---|
| 2010/0315649 A1 | 12/2010 | Yamakita | |
| 2011/0286003 A1* | 11/2011 | Ono | 356/495 |
| 2012/0092677 A1 | 4/2012 | Suehira et al. | |
| 2012/0249954 A1* | 10/2012 | Uchida | 351/206 |
| 2012/0257211 A1 | 10/2012 | Kubota et al. | |

FOREIGN PATENT DOCUMENTS

WO    WO 2010/089833    *    8/2010

OTHER PUBLICATIONS

Leitgeb, et al., Optics Express, vol. 11, No. 23, p. 3113-3121, "Real-time assessment of retinal blood flow with ultrafast acquisition by color Doppler Fourier domain optical coherence tomography" (Nov. 2003).

Stein, et al., British Journal of Ophthalmology, vol. 90(2): pp. 186-190, "A new quality evaluation parameter for optical coherence tomography" (Feb. 2006).

* cited by examiner

*Primary Examiner* — Jordan Schwartz (74) *Attorney, Agent, or Firm* — Carter, DeLuca, Farrell & Schmidt, LLP (57) ABSTRACT

Provided is an imaging apparatus for acquiring a tomographic image of an object to be inspected based on light obtained by combining return light from the object illuminated with measuring light and reference light corresponding to the measuring light, the imaging apparatus including: a reference-light amount changing unit provided in an optical path of the reference light, for changing a reference-light amount of the reference light; and a control unit for controlling the reference-light amount changing means so as to control the reference-light amount within a predetermined range and an image quality of the tomographic image within a predetermined image-quality evaluation range.

16 Claims, 6 Drawing Sheets

IMAGING APPARATUS AND IMAGING METHOD

BACKGROUND OF THE INVENTION

1. Field of the Invention

The present invention relates to an imaging apparatus and an imaging method for photographing an object to be inspected.

2. Description of the Related Art

In recent years, an apparatus using optical coherence tomography (OCT) for acquiring a tomographic image by using interference of low-coherence light (hereinafter also referred to as "OCT apparatus") has been put into practical use. The OCT is exemplified in a document tiled as "Real-time evaluation of retinal blood flow with ultrafast acquisition by color Doppler Fourier domain optical coherence tomography" in OPTICS EXPRESS 2003 Vol. 11, No. 23 P 3113-3121. The apparatus allows a tomographic image to be acquired with a resolution as high as that of a wavelength of a light entering an object to be inspected. Therefore, the tomographic image of the object to be inspected can be acquired with a high resolution. The OCT apparatus is particularly useful as a fundus examination apparatus for acquiring a tomographic image of a retina located at the back or fundus of an eye.

On the other hand, the OCT apparatus is generally based on two-dimensional scanning, and therefore has relatively long photographing time. Further, the OCT apparatus constructs the tomographic image from interference light between measuring light and reference light described later. Therefore, in order to adjust an interference-light intensity in accordance with a state of the apparatus such as a transmittance of an optical system and reflection by the object to be inspected, an adjustable neutral density filter is sometimes required to be inserted into an optical path of the reference light so as to perform adjustment in accordance with the interference-light intensity or the like.

Further, in the case where the apparatus has been used over a long period of time, a transmitted-light amount sometimes changes depending on a light amount from a light source, fine dust in an optical path, a change in coating on a lens, and the like. Also when the apparatus is used over a long period of time, the adjustment of a reference-light amount is sometimes required. The reason why the reference light is adjusted is as follows. The interference intensity can be changed by both the reference-light intensity and the measuring-light intensity. However, changing the measuring-light intensity means a change in the amount of light illuminated on the object to be inspected. Therefore, when there are restrictions on an illuminated-light amount both in terms of safety and in terms of image quality, the interference intensity is adjusted by adjusting the reference-light amount.

The adjustment described above can be experimentally implemented appropriately while a state of the apparatus is checked. However, if an inspector performs imaging after checking the state of the apparatus and implementing the adjustment, a long time is required in total, which becomes a burden on a subject.

SUMMARY OF THE INVENTION

In view of the above-mentioned problem, according to the present invention, there is provided an imaging apparatus for acquiring a tomographic image of an object to be inspected based on light obtained by combining return light from the object illuminated with measuring light and reference light corresponding to the measuring light, the imaging apparatus comprising: a reference-light amount changing unit provided in an optical path of the reference light, for changing a reference-light amount of the reference light; and a control unit for controlling the reference-light amount changing means so as to control the reference-light amount within a predetermined range and an image quality of the tomographic image within a predetermined image-quality evaluation range.

According to the present invention, the reference-light amount is automatically changed in accordance with the state of the apparatus. As a result, an adjustment time before measurement can be shortened. In this manner, the burden on the subject can be lessened.

Further features of the present invention will become apparent from the following description of exemplary embodiments with reference to the attached drawings.

BRIEF DESCRIPTION OF THE DRAWINGS

FIGS. 5A, 5B and 5C are graphs each showing a reference-light intensity.

DESCRIPTION OF THE EMBODIMENTS

Preferred embodiments of the present invention will now be described in detail in accordance with the accompanying drawings.

First Embodiment

A fundus examination apparatus of this embodiment (an example of an imaging apparatus of the present invention) controls a reference-light amount for each inspection to improve image quality for each inspection.

(Schematic Configuration of Apparatus)

Figure 2A:
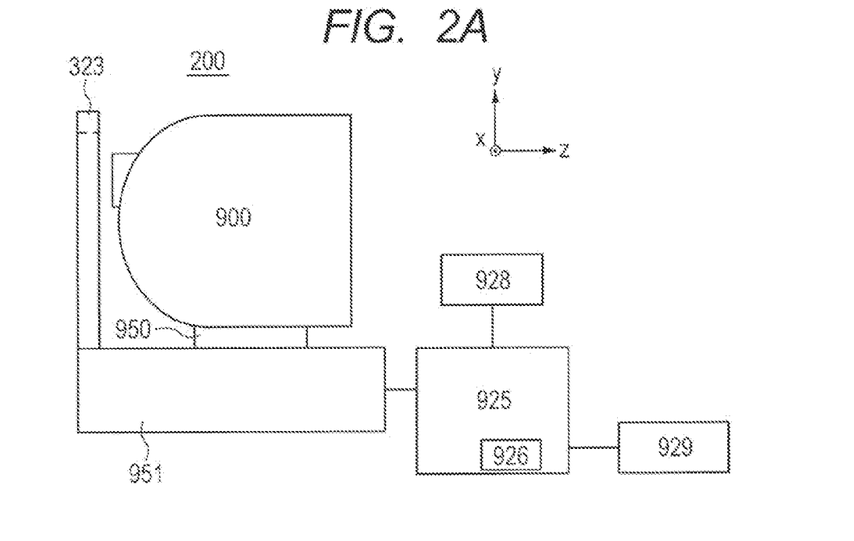
FIGS. 2A and 2B are diagrams illustrating a fundus examination apparatus according to first, second, and third embodiments of the present invention, FIG. 2A designates a side view of the fundus examination apparatus, and FIG. 2B designates configurations of measuring optical system and a spectral system of the fundus examination apparatus.

A schematic configuration of the fundus examination apparatus of this embodiment is described referring to FIG. 2A.

FIG. 2A is a side view of the fundus examination apparatus. Reference numeral 200 denotes the fundus examination apparatus, reference numeral 900 denotes an optical head which is a measurement optical system for photographing an anterior segment image as well as a two-dimensional image and a tomographic image of a fundus, and reference numeral 950 denotes a stage portion which is a moving portion that can move the optical head by using motors (not shown) in x, y, and z directions in the figure. Reference numeral 951 denotes a base portion in which a spectroscope described later is contained.

Reference numeral 925 denotes a personal computer working also as a control portion for the stage portion, which performs control on the stage portion as well as constitutes the tomographic image and the like. Reference numeral 926 denotes a hard disk, which works also as a subject information storage portion and stores a program for photographing a tomographic image and the like. Reference numeral 928 denotes a monitor as a display portion, and reference numeral 929 denotes an input portion which issues an instruction to the personal computer and specifically includes a keyboard and a mouse. Reference numeral 323 denotes a chin rest which fixes the chin and the forehead of a subject to facilitate the fixation of an eye (eye to be inspected) of the subject.

(Configurations of Measurement Optical System and Spectroscope)

Figure 2B:
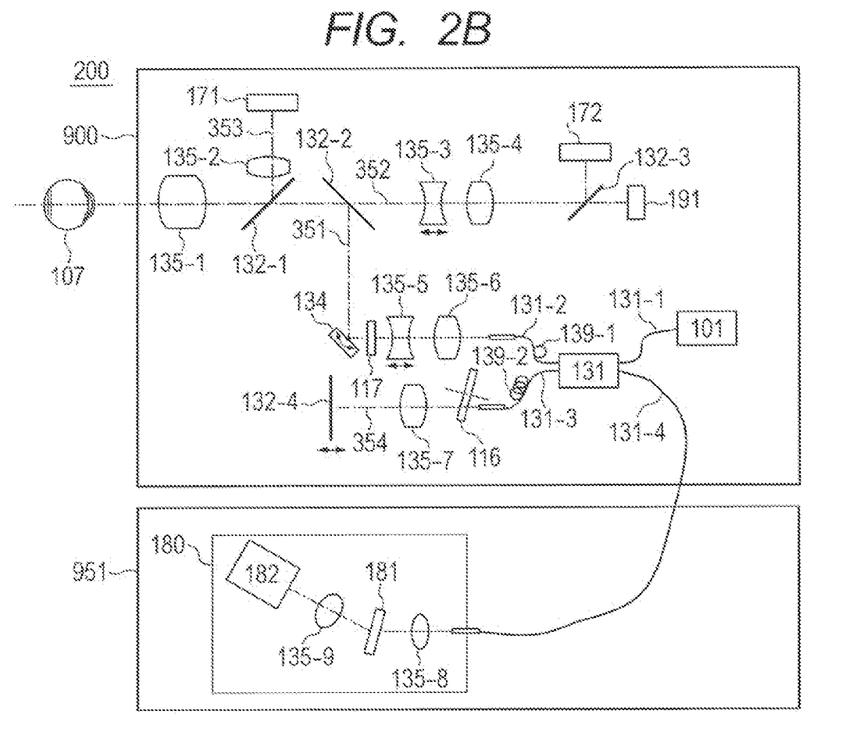

Configurations of the measurement optical system and the spectroscope of this embodiment are described referring to FIG. 2B.

First, an inside of the optical head 900 is described. An objective lens 135-1 is disposed to be opposed to an eye to be inspected 107. On the optical axis of the objective lens 135-1, a first dichroic mirror 132-1 and a second dichroic mirror 132-2 are disposed. Those dichroic mirrors separate the optical path into an optical path 351 of an OCT optical system, an optical path 352 for fundus observation and a fixation lamp, and an optical path 353 for anterior segment observation in accordance with their wavelength bands.

The optical path 352 is further split by a third dichroic mirror 132-3 into an optical path to a CCD 172 for fundus observation and an optical path to a fixation lamp 191 in accordance with their wavelength bands in the same manner as described above. Here, reference numerals 135-3 and 135-4 denote lenses, and the lens 135-3 is driven by a motor (not shown) for focusing of the fixation lamp and fundus observation. The CCD 172 has a sensitivity at a wavelength of illumination light (not shown) for fundus observation, specifically at a wavelength of approximately 780 nm. On the other hand, the fixation lamp 191 generates visible light so as to prompt the subject to stare.

In the optical path 353, reference numeral 135-2 denotes a lens and reference numeral 171 denotes an infrared CCD for anterior segment observation. This CCD 171 has a sensitivity at a wavelength of illumination light (not shown) for anterior segment observation, specifically at a wavelength of approximately 970 nm.

The optical path 351 constitutes the OCT optical system as described above, and is used for photographing a tomographic image of the fundus of the eye to be inspected 107. More specifically, the optical path 351 is used for acquiring an interference signal for forming the tomographic image. Reference numeral 117 denotes a shutter for performing irradiation of light on the eye to be inspected at the time of imaging, and reference numeral 134 denotes an XY scanner for scanning the fundus with light. The XY scanner 134 is illustrated as a single mirror but is a mirror for scanning in two directions of X and Y axes. Reference numerals 135-5 and 135-6 denote lenses, and the lens 135-5 is driven by a motor (not shown) so as to focus light from a light source 101 emerging from a fiber 131-2 connected to an optical coupler 131 on the fundus 107. By this focusing operation, light from the fundus 107 forms images simultaneously as a spot on an end of the fiber 131-2 and enters the fiber 131-2.

Next, configurations of an optical path from the light source 101, a reference optical system, and the spectroscope are described.

Reference numeral 101 denotes the light source; 132-4, a mirror; 116, neutral density filter connected to a motor (not shown) and used for changing a light amount transmitted therethrough by its rotation; 131, the above-mentioned optical coupler; 131-1 to 131-4, single-mode optical fibers connected and integrated to the optical coupler; 135-7, a lens; and 180, the spectroscope.

These elements constitute a Michelson interferometer. The light emitted from the light source 101 passes through the optical fiber 131-1 and is then split by the optical coupler 131 into measuring light on the optical fiber 131-2 side and reference light on the optical fiber 131-3 side.

The measuring light illuminates the fundus of the eye to be inspected 107 as an observation target via the above-mentioned optical path of the OCT optical system and is reflected or scattered by the retina to reach the optical coupler 131 via the same optical path. The optical paths described above function as an example of a measuring-light optical path for irradiating an object to be inspected with the measuring light to obtain reflected light (return light) from the object to be inspected.

On the other hand, the reference light reaches the mirror 132-4 through the optical fiber 131-3, the neutral density filter 116, and the lens 135-7 to be reflected thereby. Then, the reference light returns via the same optical path to reach the optical coupler 131. The optical paths described above function as an example of a reference-light optical path for irradiating the mirror 132-4 as a reference object with the reference light (reference light corresponding to the measuring light) to obtain reflected light from the reference object.

The optical coupler 131 combines the measuring light with the reference light to be interference light. Here, the interference occurs when an optical path length of the measuring light becomes almost the same as an optical path length of the reference light. The mirror 132-4 is retained in an adjustable manner in an optical axis direction by a motor (not shown) and a drive mechanism (not shown), and hence the optical path length of the reference light can be adjusted to the optical path length of the measuring light that varies depending on the eye to be inspected 107. The interference light is guided to the spectroscope 180 via the optical fiber 131-4.

In addition, reference numeral 139-1 denotes a polarization adjustment portion on the measuring light side disposed in the optical fiber 131-2. Reference numeral 139-2 denotes a polarization adjustment portion on the reference light side disposed in the optical fiber 131-3. The polarization adjustment portions include some parts in which the optical fiber is looped, and the looped part is turned about a longitudinal direction of the fiber so that the fiber is twisted. Thus, polarized states of the measuring light and the reference light can be adjusted respectively to the same state. In this apparatus, the polarized states of the measuring light and the reference light are adjusted and fixed in advance.

The spectroscope 180 is formed of lenses 135-8 and 135-9, a diffraction grating 181, and a line sensor 182. The interference light emerged from the optical fiber 131-4 becomes collimated light via the lens 135-8, and is then diffracted by the diffraction grating 181 so as to form images on the line sensor 182 via the lens 135-9.

Next, a periphery of the light source 101 is described. The light source 101 is a super luminescent diode (SLD) that is a typical low coherent light source. The center wavelength is 855 nm, and the wavelength band width is approximately 100 nm. Here, the band width is an important parameter because it affects a resolution of the acquired tomographic image in the optical axis direction.

Further, the SLD is selected as a type of the light source here, but it is sufficient as long as the light source can emit low coherent light. It is possible to use an amplified spontaneous emission (ASE) or the like. As to the center wavelength, near infrared light is suitable in view of measuring the fundus. In addition, because the center wavelength affects the resolution of the acquired tomographic image in a lateral direction, it is desired that the wavelength be as short as possible. The center wavelength is set to 855 nm because of the both reasons.

The Michelson interferometer is used as the interferometer in this embodiment, but a Mach-Zehnder interferometer may be used. In accordance with a light amount difference between the measuring light and the reference light, it is desired to use the Mach-Zehnder interferometer when the light amount difference is large, and to use the Michelson interferometer when the light amount difference is relatively small.

With the configuration described above, an example of a tomographic-image acquiring portion for acquiring the tomographic image of the object to be inspected is constituted.

Figure 6A:
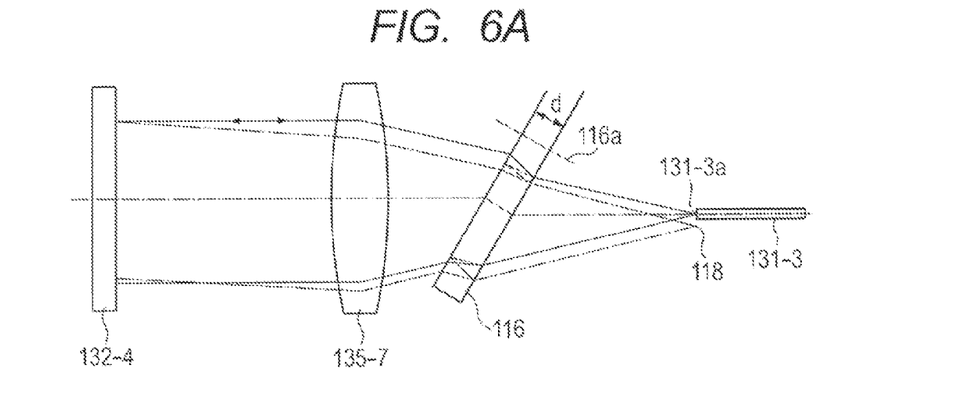
FIGS. 6A and 6B are diagrams each illustrating a reference-light optical path, FIG. 6A designates an optical path of a reference light of above specified embodiment, and FIG. 6B designates an optical path of the reference light of other example.
Figure 6B:
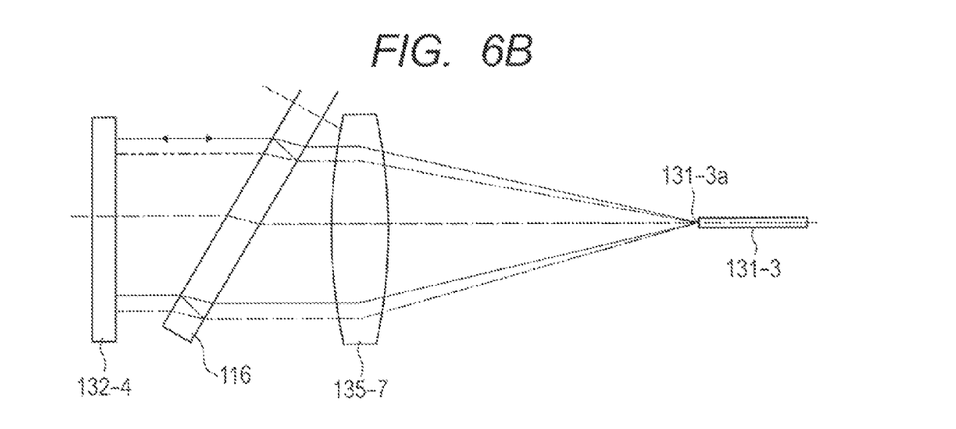

Here, the reference-light optical path is described. FIG. 6A is a diagram illustrating the reference-light optical path of this embodiment, and FIG. 6B is a diagram illustrating an example different from this embodiment.

The neutral density filter 116 is provided in front of the lens 135-7 so as to be inclined at a predetermined angle, for example, at about 10° with respect to an optical axis. The inclination is provided so that reflection from each surface of the neutral density filter 116 does not return to a fiber end 131-3a. The density of the neutral density filter 116 is changed depending on an angular position about a rotation axis 116a. In FIGS. 6A and 6B, by the rotation about the rotation axis 116a, a light amount transmitted through the neutral density filter in the figures can be changed. Moreover, by providing the neutral density filter 116 between the lens 135-7 and the fiber end 131-3a, artifact is not generated in the tomographic image.

The generation of artifact is described below. For example, in the configuration illustrated in FIG. 6B, light which is multiply-reflected for the thickness of the neutral density filter is also reflected by the mirror 132-4. Similarly to light which is not multiply-reflected, the light is also guided to the fiber end 131-3a (double-dot chain lines in FIG. 6B). An optical path length of the multiply-reflected light differs from that of the light which is not multiply-reflected, by a length which is about twice a thickness d of the neutral density filter 116. Therefore, when the multiply-reflected light interferes with the measuring light, artifact is generated on the tomographic image at a location different from a position at which the artifact is supposed to be generated. Moreover, light which has an optical path length larger than twice the thickness d, that is, four or six times larger than d or larger after repeatedly multiply-reflected is also guided to the fiber end 131-3a. Therefore, there is a possibility of generation of artifact based on such light as well.

In the configuration illustrated in FIG. 6A, the light multiply-reflected by the neutral density filter 116 has an inclination with respect to the optical axis as indicated by double-dot chain lines, and therefore forms an image not at the fiber end 131-3a but at a point 118. Accordingly, the artifact is not generated on the tomographic image.

With the neutral density filter 116 and the mechanism for rotating the neutral density filter about the rotation axis 116a described above, an example of reference-light amount changing means provided in the reference-light optical path for changing a reference-light amount of the reference light is constituted.

(Method of Photographing Tomographic Image)

A method of photographing the tomographic image using the fundus examination apparatus 200 is described. The fundus examination apparatus 200 can photograph the tomographic image of a desired part of the fundus of the eye to be inspected 107 by controlling the XY scanner 134.

First, the shutter 117 illustrated in FIG. 2B is brought into an open state to guide the measuring light to the eye to be inspected 107. The measuring light scans in an x direction in the figure so that the line sensor 182 photographs information of a predetermined number of lines in a photographing range of the fundus in the x direction. The FFT is performed on a luminance distribution on the line sensor 182 obtained at a certain position in the x direction, and information obtained by the FFT from the linear luminance distribution is converted into density or color information to be displayed on the monitor 928. This converted information is referred to as an A-scan image. A two-dimensional image on which a plurality of A-scan images are arranged is referred to as a B-scan image. After a plurality of A-scan images are photographed for constructing one B-scan image, the scan position in a y direction is moved, and the scanning in the x direction is performed again so that a plurality of B-scan images are acquired.

The plurality of B-scan images or a three-dimensional tomographic image constructed from the plurality of B-scan images is displayed on the monitor 928 so as to be used for diagnosis of the eye to be inspected by the inspector.

(Tomographic-Image Imaging Flow)

Figure 1:
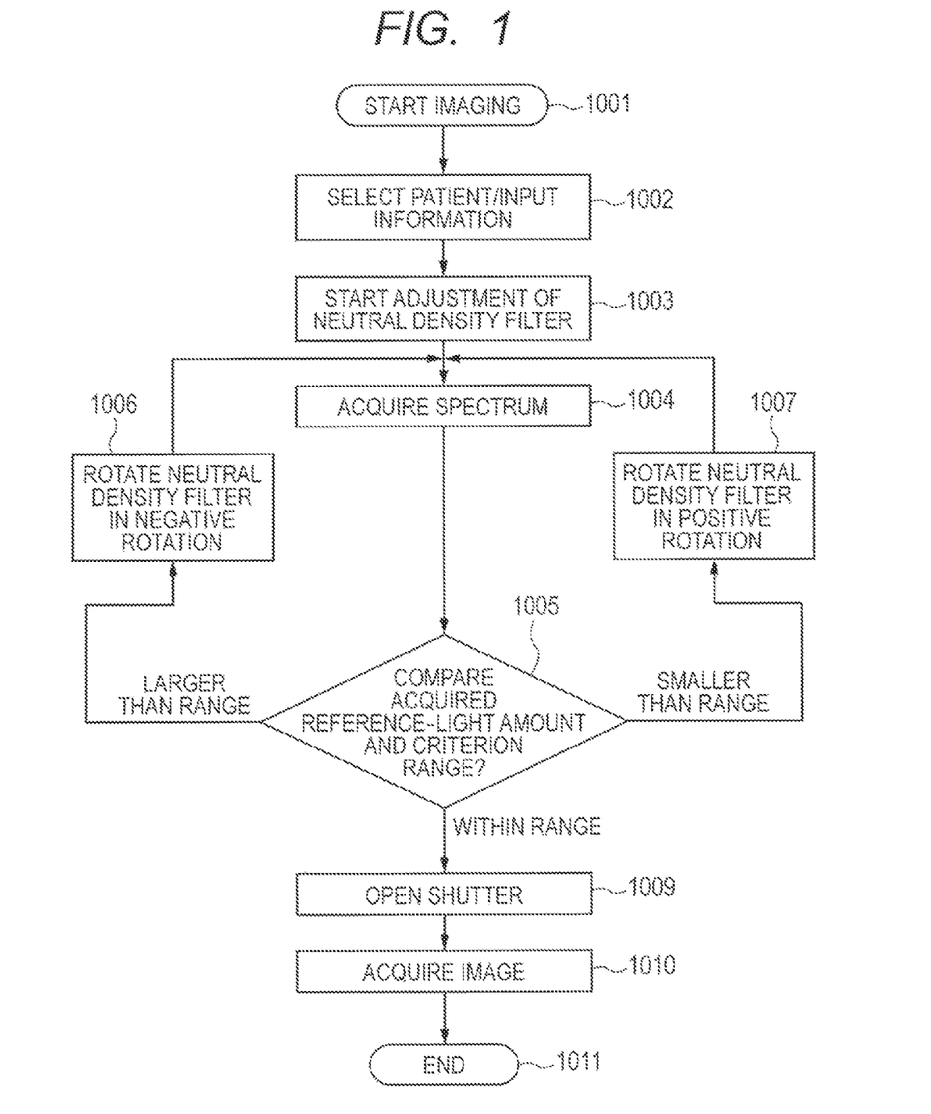
FIG. 1 is a diagram illustrating an imaging flow in a first embodiment of the present invention.

A flowchart of imaging illustrated in FIG. 1 is described in the order of steps.

In Step 1001, the imaging is started. The program for imaging is executed by the personal computer 925 to start a screen for imaging on the monitor 928. Then, the processing automatically proceeds to Step 1002.

Figure 3:
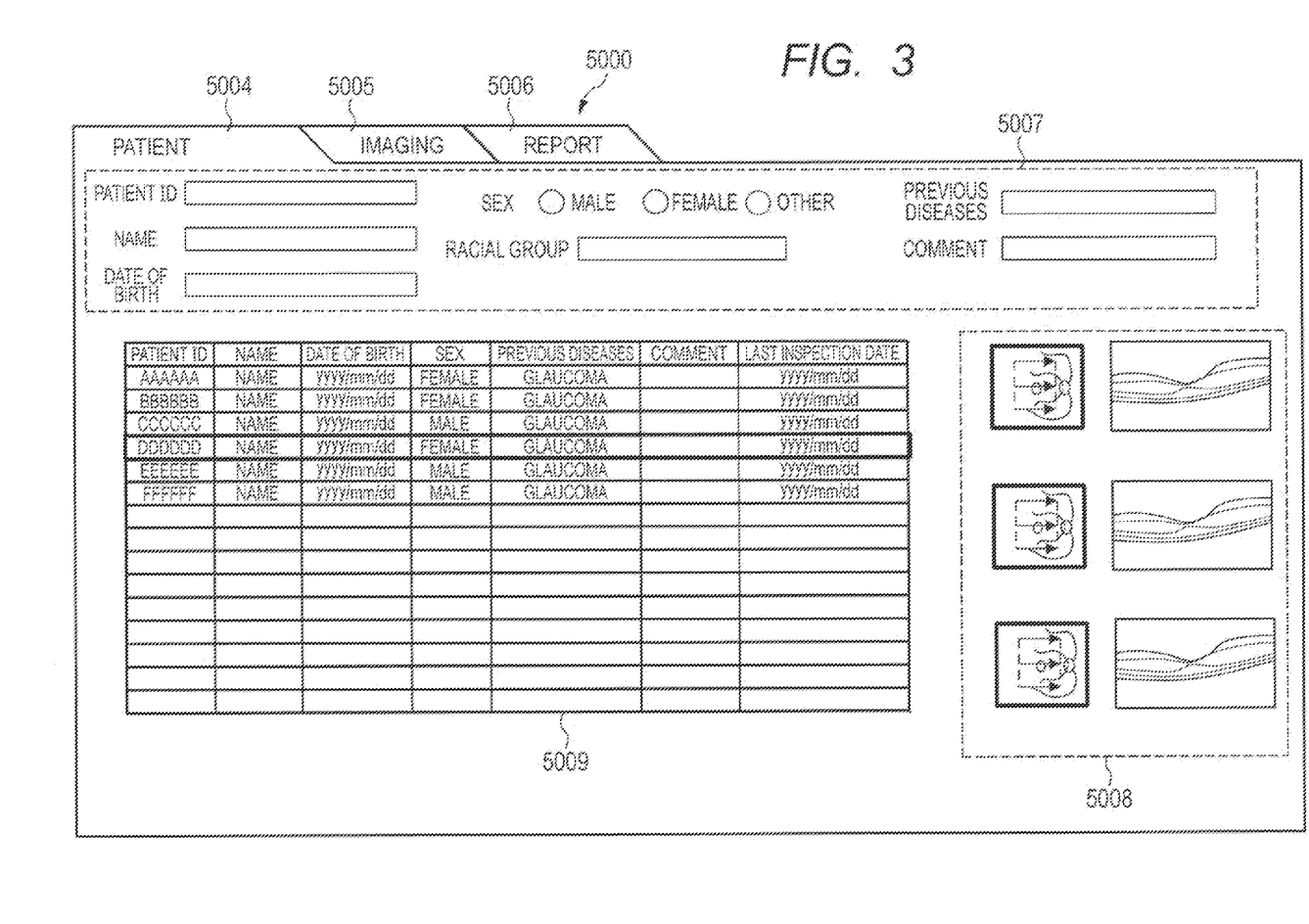
FIG. 3 is a diagram illustrating an example of a patient selection screen.

In Step 1002, a patient selection/patient-information input screen illustrated in FIG. 3 is displayed on the monitor 928. The inspector selects the patient or inputs patient information in the case of a new patient. Here, the patient selection or patient-information input is described referring to FIG. 3.

Reference numeral 5000 denotes the patient selection/patient-information input screen, reference numeral 5004 denotes a patient selection tab, reference numeral 5005 denotes an imaging selection tab, and reference numeral 5006 denotes a report-screen selection tab. Each of the screens is selected by clicking the tabs with the mouse or the like. As the current screen state, the patient selection tab denoted by reference numeral 5004 is selected. Therefore, the patient-selection screen 5000 is displayed. Reference numeral 5007 denotes a patient-information input portion, reference numeral 5008 denotes an inspection display portion for displaying previously-conducted inspection in a state in which the patient is selected, and reference numeral 5009 denotes a patient-list display portion.

A corresponding patient is selected from the patient list 5009 by an operation performed by the inspector. After the confirmation of the result of previously-conducted inspection and the like displayed in the inspection display portion 5008, the imaging selection tab 5004 is clicked with the mouse, or the imaging selection tab 5005 is clicked with the mouse after necessary information is input to the patient-information input portion 5007 in the case of the new patient. Then, the processing proceeds to Step 1003.

In Step 1003, the adjustment of the neutral density filter is started. Then, the processing automatically proceeds to Step 1004.

In Step 1004, a signal is acquired from the line sensor 182. The openable/closable shutter 117, which is an example of measuring-light amount changing means provided in a measuring-light optical path for changing the light amount of the measuring light, is in a closed state, and therefore the measuring light is not illuminated to the eye to be inspected 107 from the objective lens 135-1. Thus, the signal obtained from the line sensor 182 is a signal of the reference light. Then, the processing automatically proceeds to Step 1005.

Figure 5A:
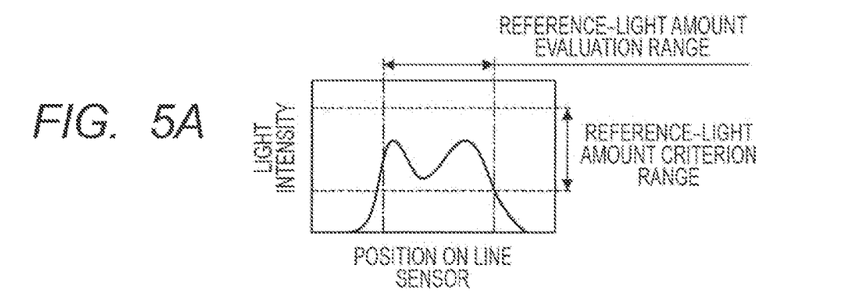
FIG. 5A shows are case where obtained signal intensity is within a criterion range.
Figure 5B:
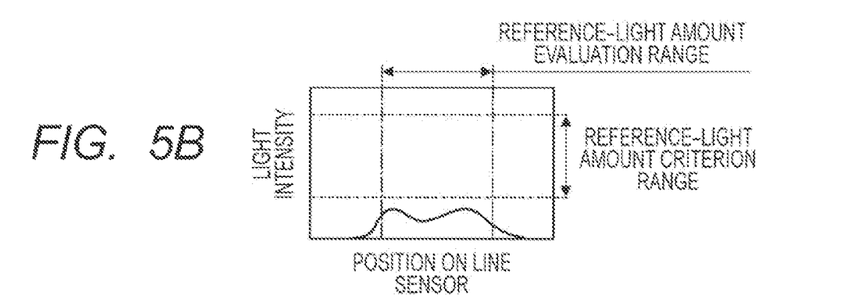
FIG. 5B shows a case where obtained signal intensity is lower than the criterion range.
Figure 5C:
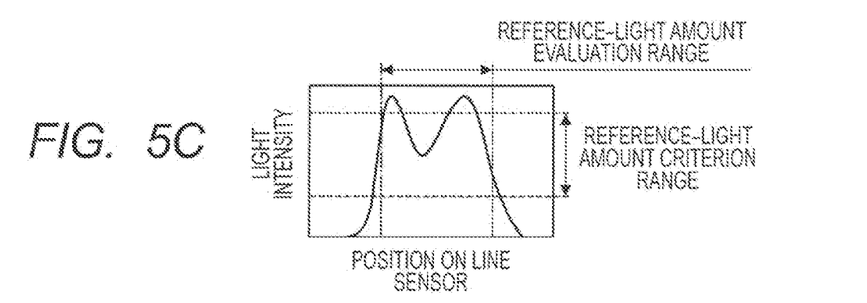
FIG. 5C shows a case where obtained signal intensity is higher than the criterion range.

In Step 1005, the signal intensity obtained by the processing described above and a criterion range are compared. The comparison is described referring to FIGS. 5A to 5C. FIG. 5A shows the case where the obtained signal intensity falls within a set criterion range, FIG. 5B shows the case where the signal intensity is lower than the criterion range, and FIG. 5C shows the case where the signal intensity is higher than the criterion range. It is determined whether or not a light intensity obtained from each of the pixels on the line sensor within a reference-light amount evaluation range in each of the figures falls within a reference-light amount criterion range shown in each of the figures. The reference-light amount criterion range, which is an example of a predetermined range, is stored in advance in the hard disk 926 which functions as an example of storage means. When there is a pixel which has a light intensity lower than the readout reference-light amount criterion range, it is determined that the reference-light amount is smaller than the criterion range. On the other hand, when there is a pixel which has a light intensity higher than the readout reference-light amount criterion range, it is determined that the reference-light amount is larger than the criterion range. When the light intensity is lower than the criterion range, a sufficiently high intensity cannot be obtained at the time of interference with the measuring light. As a result, image quality becomes unsatisfactory. On the other hand, when the light intensity is higher than the criterion range, the light intensity exceeds a light-intensity acquisition range of the line sensor 182 at the time of interference with the measuring light. As a result, an interference component cannot be sufficiently detected in the signal from the line sensor. When the light intensity falls within the criterion range, the processing automatically proceeds to Step 1009. When the light intensity is higher than the criterion range, the processing proceeds to Step 1006. When the light intensity is lower than the criterion range, the processing proceeds to Step 1007. The above-mentioned comparison between the reference-light amount and the predetermined range is executed by a module area functioning as an example of comparison means for executing the comparison in the personal computer 925.

In Step 1006, the motor (not shown) is rotated by a predetermined amount of rotation so that the light amount transmitted through the neutral density filter 116 becomes small to result in a small reference-light amount. Here, this direction of rotation is referred to as a negative direction. Then, the processing automatically returns to Step 1004 where the reference-light amount is checked again.

In Step 1007, the motor (not shown) is rotated by a predetermined amount of rotation in a positive direction opposite to the direction in Step 1006 so that the light amount transmitted through the neutral density filter 116 becomes large to result in a large reference-light amount. Then, the processing automatically returns to Step 1004 where the reference-light amount is checked again.

Specifically, in accordance with the result of comparison between the reference-light amount and the predetermined range by the comparison means described above, the personal computer 925 which is an example of control means repeats the above-mentioned operation of checking the reference-light amount by the reference-light amount changing means. Eventually, the processing proceeds to Step 1009.

In Step 1009, the XY scanner 134 is first operated. Thereafter, the light source 101 is turned on to bring the shutter 117 in the open state so as to illuminate the eye to be inspected 107 with the measuring light. In this step, in order to bring the shutter in the open state, a "measurement start" button is clearly shown on the screen, thereby prompting the inspector to perform an operation of starting the measurement. Then, the shutter 117 may be configured to be opened when the inspector double-clicks on the button with the mouse to select the measurement start. Alternatively, a measurement parameter such as a scanning pattern may be configured so as to be operated by the inspector in this step. After the shutter-opening operation, the processing automatically proceeds to Step 1010.

In Step 1010, a tomographic image is acquired. The processing automatically proceeds to Step 1011. Then, the inspection is terminated.

The imaging flow in the fundus examination apparatus of this embodiment has been described above. In this embodiment, after the inspector selects the subject or inputs the information of the subject, the flow described above is implemented.

As described above, in this embodiment, the adjustment of the reference-light amount for each inspection to bring the image quality into an optimal state can be achieved without any temporal load.

In the description given above, as the reference-light amount changing means, the neutral density filter mounted to the motor, which can change the transmitted-light amount by the rotation, is used. However, any means which can be controlled to change the light amount can be used.

Examples include:

1) a mechanism using the combination of a motor and a feed screw, which can move the fiber or the lens in the optical axis direction, so as to change a distance between the fiber end and the lens;

2) an actuator for inclining the fiber end or moving the fiber end in a direction perpendicular to the optical axis to change the return-light amount;

3) a diaphragm which can change a numerical aperture;

4) a transmissive liquid-crystal filter; and 5) the combination of two rotating polarizers.

Second Embodiment

Besides for the patient selection, a fundus examination apparatus of this embodiment also controls the timing of changing the reference-light amount for each predetermined time period (at predetermined time intervals) by including a timer for a predetermined period of time from the start of the inspection.

Specifically, in the case where the inspection on the same subject is continued after the termination of the adjustment of the neutral density filter, which follows the selection of the subject, the shutter 117 is automatically closed again after elapse of 10 minutes. In this manner, a spectrum is acquired from the line sensor 182. The reference-light amount is checked. When the reference-light amount is out of the criterion range, the neutral density filter is rotated for the adjustment. The operation for the adjustment is the same as that of the first embodiment.

With the configuration described above, the fundus examination apparatus of this embodiment can cope with a change in the apparatus occurring within a shorter period of time. It is apparent that the same effects are obtained even when the adjustment intervals to be controlled by the timer are changed by the apparatus.

Third Embodiment

A fundus examination apparatus of this embodiment assesses the image quality of the tomographic image to appropriately change the reference-light amount in accordance with the result of evaluation. In this manner, a tomographic image of good image quality can be acquired regardless of a state of the eye of the subject.

The imaging flow is different from that of the first embodiment. Therefore, different parts are described, and the description of the other parts is herein omitted.

Figure 7:
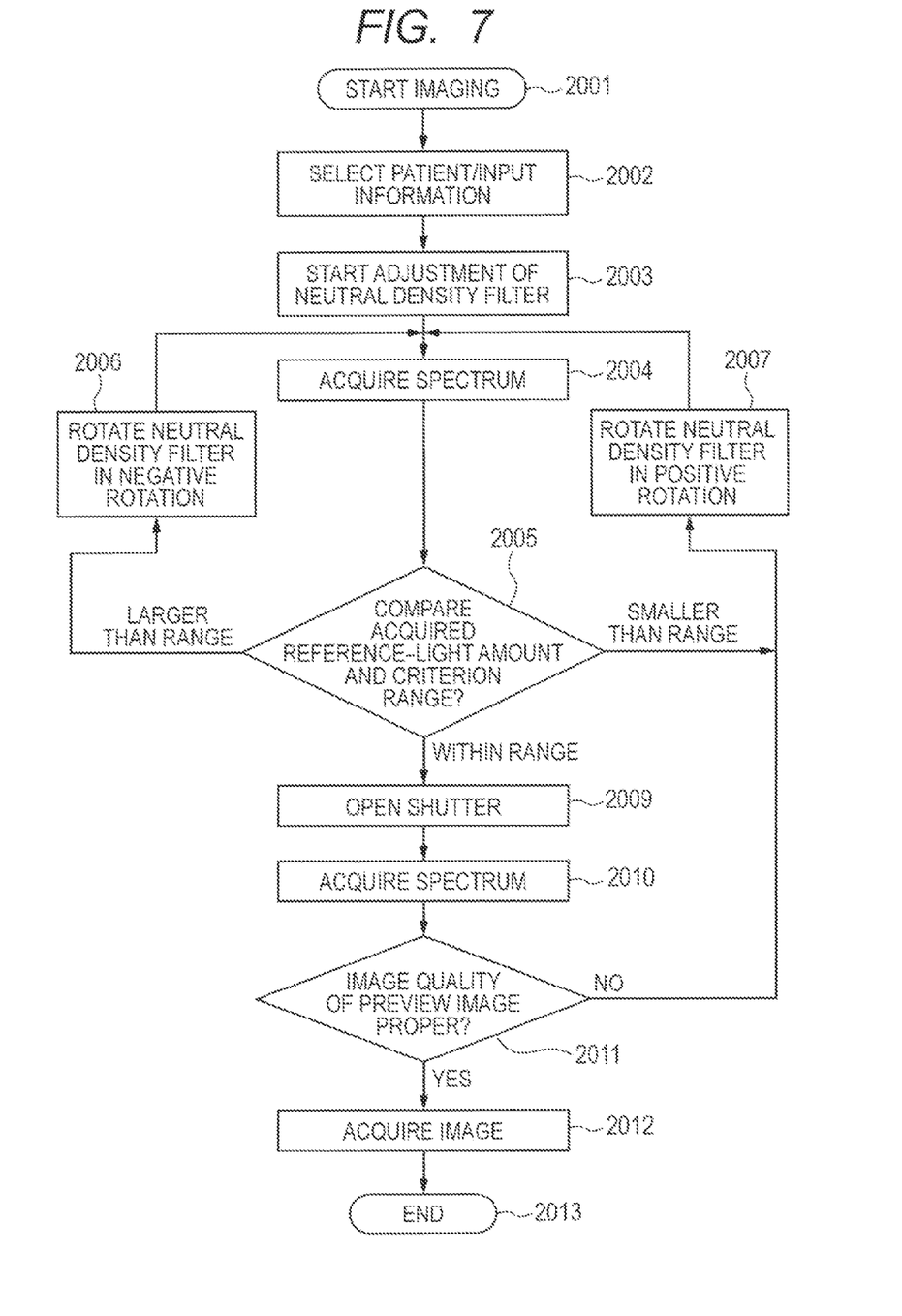
FIG. 7 is a diagram illustrating an imaging flow in the third embodiment.

The imaging flow of this embodiment is described referring to FIG. 7. The detailed description of the same steps as those of the first embodiment is herein omitted.

In Step 2001, the imaging is started. The processing automatically proceeds to Step 2002.

In Step 2002, the inspector selects the patient or inputs the patient information. The imaging screen is selected by the inspector, and then the processing proceeds to Step 2003.

In Step 2003, the adjustment of the neutral density filter is started. The processing automatically proceeds to Step 2004.

In Step 2004, the signal is acquired from the line sensor 182. The processing automatically proceeds to Step 2005.

In Step 2005, the signal intensity obtained as described above and the criterion range are compared with each other. When the signal intensity is higher than the criterion range, the processing proceeds to Step 2006. When the signal intensity is lower than the criterion range, the processing proceeds to Step 2007.

In Step 2006, the motor (not shown) is rotated by a predetermined amount of rotation so that the light amount transmitted through the neutral density filter 116 becomes small to result in a small reference-light amount. Here, this direction of rotation is referred to as the negative direction. Then, the processing automatically returns to Step 2004 where the reference-light amount is checked again.

In Step 2007, the motor (not shown) is rotated in the positive direction opposite to the direction in Step 2006 by a predetermined amount of rotation so that the light amount transmitted through the neutral density filter 116 becomes large to result in a large reference-light amount. Then, the processing automatically returns to Step 2004 where the reference-light amount is checked again.

The above-mentioned operation of checking the reference-light amount is repeated. Eventually, the processing proceeds to Step 2009.

In Step 2009, the shutter 117 is brought into the open state so that the eye to be inspected 107 is illuminated with the measuring light. Then, the processing automatically proceeds to Step 2010.

In Step 2010, a preview screen for the tomographic image is displayed. Based on the preview, the inspector adjusts a focus position and the positions of the mirrors. Then, the processing automatically proceeds to Step 2011.

In Step 2011, it is automatically determined whether or not an image-quality evaluation index, which is an example of a value indicating the image quality of the image displayed on the preview, falls within a predetermined image-quality evaluation range. Specifically, the acquired tomographic image and the predetermined range stored in advance in the hard disk 926, which is the storage means, are compared with each other. The image-quality evaluation index is described later. When the value indicating the image quality falls within the predetermined image-quality evaluation range, the processing proceeds to Step 2012. When the value indicating the image quality does not fall within the predetermined image-quality evaluation range, there is a high possibility that an interference intensity is low. Therefore, the processing proceeds to Step 2007 where the neutral density filter is adjusted so that the reference-light amount becomes large. Then, the processing proceeds to Step 2005. Steps 2005 to 2011 described above are repeated. Eventually, the processing proceeds to Step 2012.

In Step 2012, the tomographic image is acquired. Then, the processing automatically proceeds to Step 2013 where the inspection is completed.

The imaging flow in the fundus examination apparatus of this embodiment has been described above.

In the third embodiment, the comparison means execute the determination whether the image quality of the tomographic image is proper or not, in addition to the determination of the reference-light amount executed by the comparison means in the first embodiment. The comparison between the image quality evaluation index and the predetermined image quality evaluation range is executed by a module area functioning as an example of comparison means for executing the comparison in the personal computer 925. In addition, in the third embodiment, the control means controls the reference-light amount changing means so as to control the reference-light amount within the predetermined range and the image quality of the tomographic image within the predetermined image-quality evaluation range.

(Examples of Image-Quality Evaluation Index Used for Determination)

Q index: one of OCT image-quality evaluation indices, indicating a proportion of pixels effective for diagnosis in a histogram of the image. A program for calculating the Q index to compare the Q index with a target value or another value at an alignment position is image comparison means of this embodiment. The program is integrated with the above-mentioned program for imaging, and is executed in the personal computer 925 which is the apparatus control section.

Note that, a method of calculating the Q-index is described in the following literature.

[Name of Literature] British Journal of Ophthalmology, 2006; 90: pp. 186-190, "A new quality evaluation parameter for optical coherence tomography"

Here, the Q index value is used as a guide for the image quality. Besides, the use of the following image-quality evaluation indices is conceived.

SNR: a conventionally frequently used index, indicating a ratio of a maximum value of a brightness value of the image and a brightness value of background noise.

Figure 4:
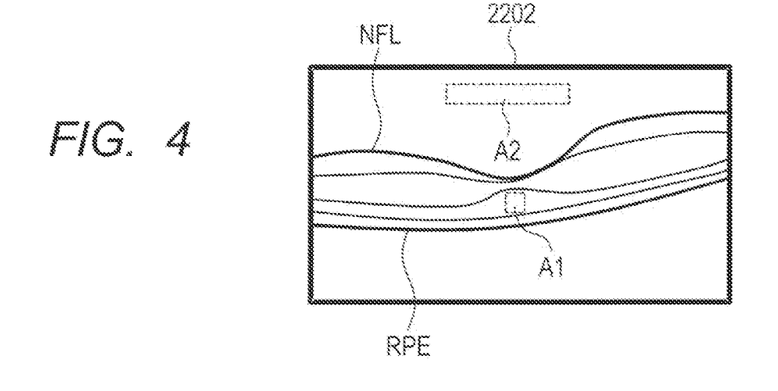
FIG. 4 is a diagram illustrating an image-quality evaluation index of a tomographic image in the third embodiment.

Local image contrast: a contrast obtained from an average brightness value of a local area included in the retina and an average brightness value of the background. An example thereof is described referring to FIG. 4. FIG. 4 illustrates a preview image of the tomographic image, indicated by reference numeral 2202. Reference symbol A1 denotes a partial area of an outer nuclear layer (ONL), which is relatively dark in a retinal layer. Reference symbol A2 denotes a partial area of the background part. The contrast is calculated from the average brightness values of the two areas.

The local contrast described above is not limited to that between the ONL and the background, but also may be a contrast between layers necessary for the diagnosis or a contrast between the layers and the background. The local contrast may also be set so as to be selectable by the inspector.

For the calculation of the local image contrast, segmentation for identifying the ONL or the like for the recognition of the area is required.

As described above, in the fundus examination apparatus of this embodiment, in addition to the first embodiment, the reference-light amount is changed depending on the state of imaging of the eye to be inspected. As a result, the tomographic image of high image quality can be acquired, for example, even for an eye to be inspected which transmits a small amount of light.

Note that in the third embodiment, both of the comparisons between the reference-light amount and the predetermined range preset for the reference-light amount, and between the image quality evaluation index of the tomographic image and the predetermined image quality evaluation range are executed. However, as further embodiment, an aspect wherein only the determination of the image quality evaluation index other than the reference-light amount may be executed to control the reference-light amount.

Other Embodiments

In addition, the present invention can be realized also by performing the following process. Specifically, software (program) for realizing the functions of the above-mentioned embodiments is supplied to a system or an apparatus via a network or various storage media, and a computer (CPU, MPU, or the like) of the system or the apparatus reads and executes the program.

The present invention is not limited to the embodiments described above. The present invention can be carried out with various modifications and changes without departing from the gist of the present invention. For example, although the case where the object to be inspected is the eye has been described in the embodiments described above, the present invention is applicable to objects to be inspected other than the eye, such as skin or an internal organ. In this case, the present invention has a mode as medical equipment other than an ophthalmologic apparatus, for example, an endoscope. Therefore, it is desired that the present invention be comprehended as an inspection apparatus exemplified as the ophthalmologic apparatus and the eye to be inspected be comprehended as a mode of the object to be inspected.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-190597, filed Aug. 30, 2012, which is hereby incorporated by reference herein in its entirety.

What is claimed is:

1. An imaging apparatus for acquiring a tomographic image of an object to be inspected, the imaging apparatus comprising;
    an illumination source;
    a beam splitting unit to split light from the illumination source into measuring light that illuminates the object to be inspected and reference light;
    a detecting unit to detect combined light obtained by combining return light from the object illuminated with measuring light and the reference light;
    a reference-light amount changing unit provided in an optical path of the reference light, for changing a reference-light amount of the reference light; and
    a control unit for controlling the reference-light amount changing unit so that the reference-light amount is changed within a predetermined range and an image quality of the tomographic image is changed within a predetermined image quality evaluation range.

2. An imaging apparatus according to claim 1, further comprising a comparison unit for comparing the reference-light amount and the predetermined range,
    wherein, when the comparison unit provides a comparison result that the reference-light amount is out of the predetermined range, the control unit controls the reference-light amount changing unit so that the reference-light amount falls within the predetermined range.

3. An imaging apparatus according to claim 1, further comprising a measuring-light amount changing unit provided in an optical path of the measuring light, for changing a light amount of the measuring light illuminating the object,
    wherein, when the reference-light amount falls within the predetermined range and the image quality of the tomographic image falls within the predetermined image quality evaluation range, the control unit controls the measuring-light amount changing unit so that the measuring light is illuminated to the object.

4. An imaging apparatus according to claim 3, wherein the measuring-light amount changing unit comprises an openable/closable shutter, and
    wherein in a case that the shutter is in a closed state, when the reference-light amount falls within the predetermined range and the image quality of the tomographic image falls within the predetermined image quality evaluation range, the control unit opens the shutter.

5. An imaging apparatus according to claim 1, further comprising a tomographic image acquiring unit for acquiring the tomographic image when the reference-light amount falls within the predetermined range and the image quality of the tomographic image falls within the predetermined image quality evaluation range.

6. An imaging apparatus for acquiring a tomographic image of an object to be inspected, the imaging apparatus comprising:
    an illumination source;
    a beam splitting unit to split light from the illumination source into measuring light that illuminates the object to be inspected and reference light;
    a detecting unit to detect combined light obtained by combining return light from the object illuminated with measuring light and the reference light;
    a reference-light amount changing unit provided in an optical path of the reference light, for changing a reference-light amount of the reference light; and
    a control unit for controlling, in a case that an image quality of the tomographic image is out of a predetermined image quality evaluation range, the reference-light amount changing unit so that the image quality of the tomographic image is changed within the predetermined image quality evaluation range.

7. An imaging apparatus according to claim 6, further comprising a tomographic-image acquiring unit for acquiring the tomographic image when the image quality of the tomographic image falls within the predetermined image quality evaluation range.

8. An imaging apparatus according to claim 6, further comprising a comparison unit for comparing the image quality of the tomographic image and the predetermined image quality evaluation range, wherein, when the comparison unit provides a comparison result that the image quality of the tomographic image is out of the predetermined image quality evaluation range, the control unit controls the reference-light amount changing unit so that the reference-light amount becomes large.

9. An imaging apparatus according to claim 1, wherein the reference-light amount changing unit is provided in the optical path of the reference light so as to be inclined at a predetermined angle.

10. An imaging apparatus according to claim 2, wherein, after an inspector selects a subject or inputs information of the subject, the comparison unit compares the reference-light amount and the predetermined range with each other.

11. An imaging apparatus according to claim 2, wherein the comparison unit compares the reference-light amount and the predetermined range with each other at predetermined time intervals.

12. An imaging method for acquiring a tomographic image of an object to be inspected, the imaging method comprising;

splitting light from an illumination source into measuring light that illuminates the object to be inspected and reference light;

detecting combined light obtained by combining return light from the object illuminated with measuring light and the reference light; and changing a reference-light amount of the reference light so that the reference-light amount is changed within a predetermined range and an image quality of the tomographic image is changed within a predetermined image quality evaluation range.

13. A non-transitory tangible medium having recorded thereon a program for controlling a computer to execute each of the steps of the imaging method according to claim 12.

14. An imaging method for acquiring a tomographic image of an object to be inspected, the imaging method comprising:

splitting light from an illumination source into measuring light that illuminates the object to be inspected and reference light;

detecting combined light obtained by combining return light from the object illuminated with measuring light and the reference light; and changing, in a case that an image quality of the tomographic image is out of a predetermined image quality evaluation range, a reference-light amount of the reference light so that the image quality of the tomographic image is changed within the predetermined image quality evaluation range.

15. A non-transitory tangible medium having recorded thereon a program for controlling a computer to execute each of the steps of the imaging method according to claim 14.

16. An imaging apparatus according to claim 1, further comprising a polarization adjustment portion for adjusting the polarization of the reference light wherein the reference-light amount changing unit changes the reference-light amount, independent from the polarization adjustment of the reference light.

* * * * *